ROSE PLANT
Filed Sept. 6, 1974
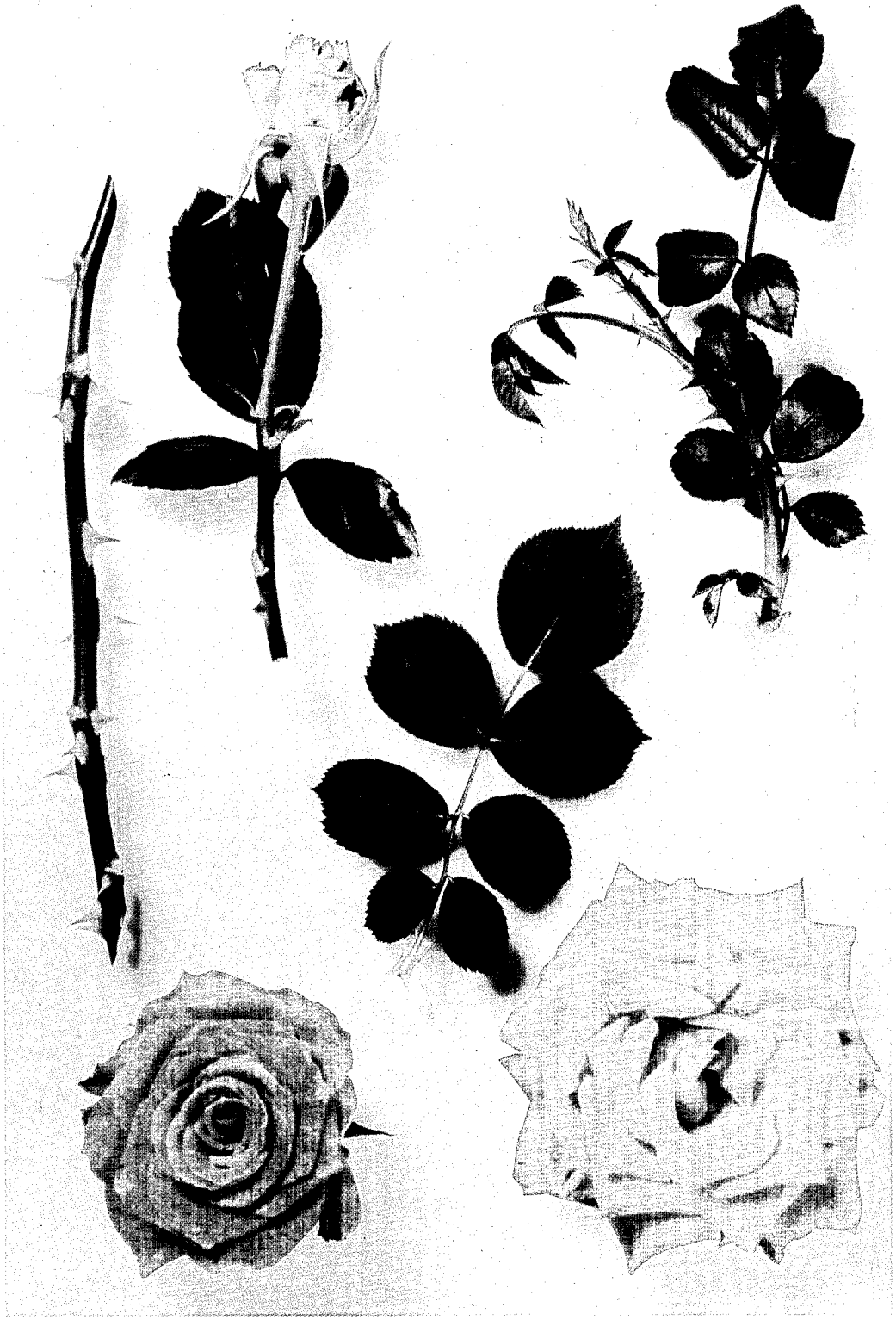

United States Patent

Plant Pat. 3,779
Patented Sept. 9, 1975

3,779
ROSE PLANT

William A. Warriner, Tustin, Calif., assignor to Jackson and Perkins Company, Medford, Oreg.

Filed Sept. 6, 1974, Ser. No. 503,778
Int. Cl. A01h *5/00*
U.S. Cl. Plt.—20 1 Claim The present invention relates to a new and distinct cultivar of rose plant of the hybrid tea class, originated by me by crossing two unnamed cultivars of roses.

The primary objective of this breeding was to produce a new cultivar of the hybrid tea class with very double (many petalled) flowers of a bright vermilion-like color on vigorous, freely blooming plants.

This objective was fully achieved along with other desirable and distinct improvements as evidenced by the following unique combination of characteristics which are outstanding in the new cultivar and which distinguish it from its parents as well as from all other cultivars of which I am aware:

1. A vigorous, well branched, upright habit of growth.
2. Broadly oval, nearly round, leaflets of leathery texture.
3. Relatively short, blunt tipped, buds opening into high centered imbricated open flowers.
4. Open color near, but darker and more vivid than Wilson's Vermilion.
5. Very little fragrance.

Asexual reproduction of my new cultivar by budding as performed at Wasco, Calif., shows that the aforementioned characteristics come true to form and are established and transmitted through succeeding propagations.

The accompanying illustration shows typical specimens of the vegetative growth and flowers of the new cultivar in different stages of development, depicted in color as nearly true as it is reasonably possible to make the same in a color illustration of this character.

The following is a detailed description of my new rose variety with color terminology in accordance with *Wilson's Horticultural Color Chart,* except where ordinary dictionary significance of color is indicated.

Parentage: Seedling.
*Seed Parent.*—South Seas.
*Pollen Parent.*—61–18632.
Classification:
*Botanic.*—Rosa hybrid.
*Commercial.*—Hybrid tea.

*Flower*

Observations were made at Irvine, Calif. in March from plants grown in a greenhouse.

Blooming habit: Rercurrent—continuous.
Bud:
*Size.*—1½ inches when petals start to unfurl.
*Form.*—Short, blunt top, globular.
*Color.*—When sepals first divide, near Geranium Lake (20/1). When half blown, upper side of petals slightly darker than Vermilion (18); lower side of petals near but darker than Carmine (21).
*Sepals.*—Color: Outer surface slightly lighter than Scheeles Green (860/3). Shaded near outer edges Scheeles Green (860/1) with numerous stipitate glands. Inner surface Scheeles Green (860/2) only lightly tomentose. Three appendaged sepals lightly appendage. Two unappendaged sepals hairy edged.
*Receptacle.*—Color: Near Scheeles Green (860/3) shaded on side exposed to sun with Garnet Brown (00918/3). Shape: Funnel. Size: Large, broad. Surface: Smooth.

*Peduncle.*—Length: Medium. Surface: Slightly prickly. Color: Light green, shaded with Garnet Brown (00918/3). Strength: Stiff, erect.
*Opening.*—Slowly—outer petals curl outwardy.
Bloom:
*Size.*—Large. Average open size 3½ to 4 inches.
*Borne.*—Singly and sometimes several together.
*Stems.*—Long.
*Form.*—When first open—high centered. Permanence—retains its form to the end.
*Petalage.*—Number of petals under normal conditions, 40–50.
*Color.*—Center of flower: Upper side of petals near Vermilion (18/1). Reverse side of petals near Carmine (21/1). Base of petals small area near Naples Yellow (403/3). General tonality from a distance Vermilion (18). Variegations: Occasionally a white streak will occur in center of some petals.
*Discoloration.*—At end of firct day—none. Third day—gradually lightens to a lighter Vermilion (18/1) or (18/2).
*Fragrance.*—Very slight if any.
*Petals.*—Texture: Thick.
*Shape.*—Broad, oval.
*Form.*—Tips slightly recurved.
*Arrangement.*—Imbricated.
*Petaloids in center.*—Few.
*Persistence.*—Drop off cleanly.
*Lastingness.*—On the plant—long. As cut flower—long.
Reproductive parts:
*Anthers.*—Large. Color—near Maize Yellow (607). Arrangment—regular round styles.
*Filaments.*—Color—near Carmine Rose (621/2).
*Pollen.*—Gold yellow.
*Styles.*—Color—near Claret Rose (021).
*Stigmas.*—Color—near white.

*Plant*

Form: Bush.
Growth: Vigorous, upright, branching.
Foliage: Number of leaflets on normal mid-stem leaves, 5 or 7.
*Size.*—Large.
*Quantity.*—Normal.
*Color.*—New foliage: Garnet Brown (00918/2). Old foliage: near Spinach Green (0960/2).
Leaflets:
*Shape.*—Broad, oval.
*Texture.*—Upper side—leathery.
*Edge.*—Serrated.
*Serration.*—Single, small.
*Petiole (rachis).*—Color—Green. Underside—Few prickles.
*Stipules.*—Long, bearded.
*Disease Resistance.*—Resistant to mildew under normal growing conditions at Irvine, Calif.
Wood:
*New wood.*—Color—Reddish. Bark—smooth.
*Old wood.*—Color—green. Bark—smooth.
Prickles:
*Quantity.*—On main stalks from base—ordinary. On laterals from stalk—ordinary.
*Form.*—Broad base, hooked downwardly.
*Color when young.*—Brown.
*Position.*—Irregular.
Small prickles:
*Quantity.*—On main stalks—few. On laterals—few.
*Color.*—Brown.

I claim:

1. A new and distinct cultivar of rose plant of the hybrid tea class, substantially as herein shown and described, characterized particularly as to novelty by the unique combination of a well branched, vigorous plant, nearly round leaflets, short, blunt buds that open into very double imbricated blooms of a color near Wilson's Vermilion with little or no fragrance.

No references cited.

ROBERT E. BAGWILL, Primary Examiner